US012782363B2

(12) United States Patent
Kim et al.

(10) Patent No.: US 12,782,363 B2
(45) Date of Patent: Nov. 3, 2026

(54) ASSESSMENT METHODS AND DIAGNOSTIC KIT FOR PREDICTING ACUTE ANTIDEPRESSANT RESPONSE AND REMISSION IN PATIENTS WITH DEPRESSIVE DISORDERS USING MULTIMODAL SERUM BIOMARKERS

(71) Applicant: INDUSTRY FOUNDATION OF CHONNAM NATIONAL UNIVERSITY, Gwangju (KR)

(72) Inventors: Jae Min Kim, Gwangju (KR); Hee Ju Kang, Gwangju (KR)

(73) Assignee: INDUSTRY FOUNDATION OF CHONNAM NATIONAL UNIVERSITY, Gwangju (KR)

( * ) Notice: Subject to any disclaimer, the term of this patent is extended or adjusted under 35 U.S.C. 154(b) by 548 days.

(21) Appl. No.: 17/855,474

(22) Filed: Jun. 30, 2022

(65) Prior Publication Data

US 2023/0213530 A1 Jul. 6, 2023

(30) Foreign Application Priority Data

Dec. 30, 2021 (KR) ........................ 10-2021-0192972

(51) Int. Cl.
*G01N 33/68* (2006.01)
*G01N 33/74* (2006.01)

(52) U.S. Cl.
CPC . *G01N 33/6869* (2013.01); *G01N 2333/5412* (2013.01); *G01N 2333/545* (2013.01)

(58) Field of Classification Search
CPC ..... G01N 2333/5412; G01N 2333/545; G01N 2333/4737; G01N 2800/304; G01N 2800/52
See application file for complete search history.

(56) References Cited

U.S. PATENT DOCUMENTS

2012/0178118 A1* 7/2012 Pi ........................ G01N 33/6848
435/23

FOREIGN PATENT DOCUMENTS

KR 10-2214214 B1 2/2021
WO WO-2016160484 A1 * 10/2016 ......... G01N 33/6893

OTHER PUBLICATIONS

Carrero et al. hsCRP Level and the Risk of Death or Recurrent Cardiovascular Events in Patients With Myocardial Infarction: a Healthcare-Based Study. Journal of the American Heart Association. 8: e012638; Published: Jun. 4, 2019 (Year: 2019).*
Strawbridge et al. European Neuropsychopharmacology 25: 1532-1543; Published: Jun. 20, 2015 (Year: 2015).*
Carboni et al. Translational Psychiatry. 9: 182; Published: Aug. 2, 2019 (Year: 2019).*
Corradi et al. Revista De Medicina. 96 (2): 103-115; Published: Sep. 6, 2017 (Year: 2017).*
Kofod et al. European Neuropsychopharmacology 54: 116-125; Published: Sep. 29, 2021 (Year: 2021).*
Haapakoski et al. Brain, Behavior, and Immunity. 49: 206-215; Published: Jun. 9, 2015 (Year: 2015).*
Rapaport et al. Molecular Psychiatry. 21: 71-79; Published: Mar. 24, 2015 (Year: 2015).*
Kim et al. Brain, Behavior, and Immunity. 104: 65-73: Published: May 23, 2022 (Year: 2022).*
Merriam-Webster Dictionary. Quartile definition. Accessed Jan. 2, 2025 (Year: 2025).*
Kim et al. Comprehensive Psychiatry. 95: 152140; Published: Oct. 19, 2019 (Year: 2019).*
Cattaneo et al. Neuropsychopharmacology. 38: 377-385; Published: Sep. 19, 2012 (Year: 2012).*
Rahmouni et al. Recent Progress in Hormone Research. 59: 225-244; Published: 2004 (Year: 2004).*
Dremencov et al. Biological Psychiatry. 61(5): 671-678; Published: Aug. 24, 2006 (Year: 2006).*
Nahas et al. Canadian Family Physician. 57(6): 659-663; Published: Jun. 2011 (Year: 2011).*
Shelton et al. CNS Drugs. 24: 131-161: Published: Aug. 29, 2012 (Year: 2012).*
Niciu et al. Annual Review of Pharmacology and Toxicology. 54: 119-139; Published: Jan. 2014 (Year: 2014).*

* cited by examiner

*Primary Examiner* — Gregory S Emch
*Assistant Examiner* — Katherine Ann Holtzman
(74) *Attorney, Agent, or Firm* — The PL Law Group, PLLC

(57) ABSTRACT

A method for predicting antidepressant treatment response and acute prognosis for depressed patients according to an embodiment of the present disclosure includes measuring a concentration of an antidepressant treatment response prediction biomarker contained in a biological sample of a depressed patient at baseline and determining whether there is an acute phase remission, depending on the measured concentration of the antidepressant treatment response prediction marker.

6 Claims, 1 Drawing Sheet

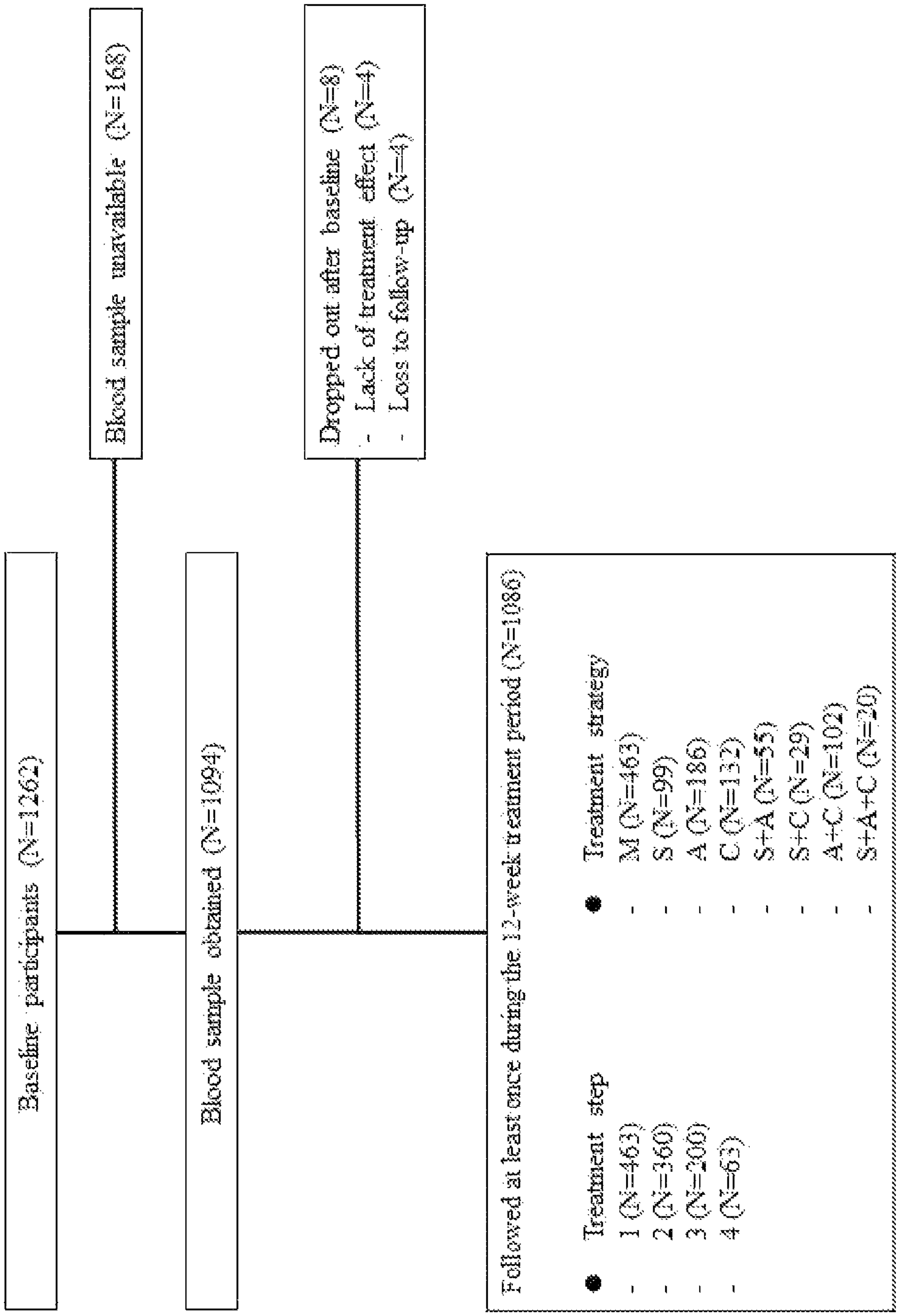
Baseline participants (N=1262)
Blood sample unavailable (N=168)
Blood sample obtained (N=1094)
Dropped out after baseline (N=8)
- Lack of treatment effect (N=4)
- Loss to follow-up (N=4)
Followed at least once during the 12-week treatment period (N=1086)
● Treatment step
- 1 (N=463)
- 2 (N=360)
- 3 (N=200)
- 4 (N=63)
● Treatment strategy
- M (N=463)
- S (N=99)
- A (N=186)
- C (N=132)
- S+A (N=55)
- S+C (N=29)
- A+C (N=102)
- S+A+C (N=20)

ASSESSMENT METHODS AND DIAGNOSTIC KIT FOR PREDICTING ACUTE ANTIDEPRESSANT RESPONSE AND REMISSION IN PATIENTS WITH DEPRESSIVE DISORDERS USING MULTIMODAL SERUM BIOMARKERS

CROSS REFERENCE TO RELATED APPLICATION AND CLAIM OF PRIORITY

This application claims the benefit under 35 USC § 119 of Korean Patent Application No. 10-2021-0192972, filed on Dec. 30, 2021, in the Korean Intellectual Property Office, the entire disclosure of which is incorporated herein by reference for all purposes.

BACKGROUND

1. Field of the Invention

The present invention relates to a diagnostic method for predicting antidepressant treatment response and prognosis for depressed patients, and more particularly to assessment methods for predicting acute antidepressant response and remission in patients with depressive disorders by examining biomarkers contained in biological samples of depressed patients at baseline, and a diagnostic kit.

2. Description of the Related Art

Depression is a common psychiatric disorder and one of the leading causes of disability worldwide, particularly in working age populations. Depression is a chronic disease that often recurs and sometimes has serious consequences that can even lead to suicide. In addition, it is known that depression shows various clinical symptoms and course, treatment response is different, and genes related to various neurobiological mechanisms are also diverse.

Antidepressant prescription is the most common treatment modality for moderate and severe major depressive disorder (MDD). However, pharmacological treatment outcomes in patients with MDD are not satisfactory.

Most antidepressants are drugs that modulate the activity of dopamine and serotonin in the brain, wherein the most commonly used antidepressants include escitalopram, sertraline, paroxetine, fluoxetine, mirtazapine, bupropion, venlafaxine, duloxetine, desvenlafaxine, vortioxetine, and agomelatine, etc. These antidepressants can be used in combination depending on the treatment response, or can be used together with various mood stabilizers and antipsychotic drugs, wherein the various mood stabilizers include Lithium, thyroid hormone, chlorpromazine, perphenazine, loxapine, trifluoperazine, haloperidol, bromperidol, pimozide, sulpiride clozapine, risperidone, olanzapine, quetiapine, etc. During these drug treatments, patients may experience adverse effect of these drugs such as headache, insomnia/hypersomnia, gastrointestinal disorders such as sweating etc., heartburn, tremors, agitation, vertigo, muscle tension, etc. and may experience exacerbation of symptoms due to the lack of drug effect such as hyperactivity, aggression, hostility, negativism, hallucinations, acute delusions, insomnia, poor appetite or food refusal, social withdrawal or isolation. These changes can cause the patient to stop taking the drug, which leads to the failure of the drug treatment. Therefore, there is a need to improve the treatment results of antidepressants for depression.

Although extensive research has been carried out, the blood biomarkers suggested by the previous studies have been of limited use in clinical practice for various reasons. First, predictive values of individual biomarkers have been unsatisfactory. An investigation of multiple biomarkers covering various functional systems in combination might increase the predictive ability but this approach has not yet been evaluated. Second, most findings have been drawn from randomized controlled trial samples with limited generalizability to real world clinical populations. Third, although most treatment guidelines suggest that depression treatment should continue over six months, most studies not only evaluated the acute treatment response, but did not provide biomarkers that could accurately predict the treatment response and its prognosis.

Therefore, there is a need to develop new biomarkers that are sufficiently effective as a marker to predict the treatment response and acute prognosis after antidepressant prescription to depressed patients.

SUMMARY

The present inventors have performed research to predict acute antidepressant response and remission in patients with depressive disorders based on the concentration of specific biomarkers present in biological samples of depressed patients, thus culminating in the present invention.

Accordingly, an aspect of the present invention is to provide an assessment method for predicting antidepressant treatment response and acute prognosis for depressed patients at baseline by specifying one or more biomarkers and cut-off levels for antidepressant treatment response and acute prognosis in depressed patients, which may contribute to a decision-making process with regard to therapeutic drugs or treatment methods. This is because it was confirmed that there was an improvement in the possibility of acute phase remission due to the treatment response after antidepressant administration through an experiment when a specific biomarker was present at a specific concentration, that is, below the cut-off level, in the biological sample of depressed patients at the baseline.

Another aspect of the present invention is to provide a diagnostic kit for predicting antidepressant treatment response and acute prognosis for depressed patients by measuring a concentration of one or more biomarkers for antidepressant treatment response prediction contained in a biological sample of a depressed patient at baseline, in which the antidepressant treatment response prediction biomarkers include a high-sensitivity C-reactive protein (hsCRP), interleukin-1 beta (IL-1β), interleukin-6 (IL-6), and leptin, and providing a customized treatment strategy to each patient based on the prediction result, thus providing clinical usefulness.

The aspects of the present invention are not limited to the foregoing, and it is to be understood that other aspects not mentioned herein can be clearly anticipated by those skilled in the art from the following description.

In order to accomplish one or more of the above aspects, the present invention provides a method for predicting antidepressant treatment response and acute prognosis for depressed patients, including measuring a concentration of an antidepressant treatment response prediction biomarker contained in a biological sample of a depressed patient at baseline; and determining whether there is an acute phase remission, depending on the measured concentration of the antidepressant treatment response prediction marker.

In an exemplary embodiment, the antidepressant treatment response prediction biomarker is one or more markers selected from the group consisting of a high-sensitivity C-reactive protein (hsCRP), interleukin-1 beta (IL-1p), interleukin-6 (IL-6), and leptin.

In an exemplary embodiment, the determining is performed by comparing the measured concentration of the antidepressant treatment response prediction biomarker with a preset cutoff level thereof, wherein it is determined that there is a probability of an acute phase remission when the measured concentration is lower than the preset cutoff level.

In an exemplary embodiment, when the antidepressant treatment response prediction biomarker is the hsCRP, the preset cutoff level is 0.61 mg/dL, when the antidepressant treatment response prediction biomarker is the IL-1p, the preset cutoff level is 1.13 pg/mL, when the antidepressant treatment response prediction biomarker is the IL-6, the preset cutoff level is 1.45 pg/mL, and when the antidepressant treatment response prediction biomarker is the leptin, the preset cutoff level is 4.39 ng/mL.

In an exemplary embodiment, in the determining, as the number of the antidepressant treatment response prediction biomarkers, each exhibiting the concentration lower than the preset cutoff level thereof, increases, the probability of the acute phase remission increases compared to a reference level.

In an exemplary embodiment, in the determining, when the number of the antidepressant treatment response prediction biomarkers, each exhibiting the concentration lower than the preset cutoff level thereof, is one, the probability of the acute phase remission increases 2.3 times compared to the reference level, and when the number of the antidepressant treatment response prediction biomarkers, each exhibiting the concentration lower than the preset cutoff level thereof, is four, the probability of the acute phase remission increases 7.5 times compared to the reference level.

In addition, the present invention provides a method for predicting antidepressant treatment response and acute prognosis for depressed patients, including measuring a concentration of each of four antidepressant treatment response prediction biomarkers contained in a biological sample of a depressed patient at baseline, the four antidepressant treatment response prediction biomarkers including a high-sensitivity C-reactive protein (hsCRP), interleukin-1 beta (IL-1β), interleukin-6 (IL-6), and leptin; and determining whether there is an acute phase remission, depending on the measured concentration of each of the four antidepressant treatment response prediction biomarkers.

In an exemplary embodiment, the determining includes allocating a reference point by: for each of the respective measured concentrations of the four antidepressant treatment response prediction biomarkers, a reference point of 1 is allocated when the measured concentration is lower than the preset cutoff level thereof and a reference point of 0 is allocated when the measured concentration is higher than the preset cutoff level thereof;

calculating a multi-biomarker score according to Formula 1 below:

$$\text{multi-biomarker score}=0.694\times A+0.424\times B+0.056\times C+0.495\times D \qquad \text{[Formula 1]}$$

wherein A is the reference point of the hsCRP, B is the reference point of the IL-1β, C is the reference point of the IL-6, and D is the reference point of the leptin; and determining a probability of an acute phase remission by finding a quartile in which the calculated multi-biomarker score is located.

In an exemplary embodiment, when the antidepressant treatment response prediction biomarker is the hsCRP, the preset cutoff level is 0.61 mg/dL, when the antidepressant treatment response prediction biomarker is the IL-1β, the preset cutoff level is 1.13 pg/mL, when the antidepressant treatment response prediction biomarker is the IL-6, the preset cutoff level is 1.45 pg/mL, and when the antidepressant treatment response prediction biomarker is the leptin, the preset cutoff level is 4.39 ng/mL.

In an exemplary embodiment, when the multi-biomarker score is within a range of 0 to 0.480, the score is located in the first quartile; when the multi-biomarker score is within a range of 0.481 to 0.750, the score is located in the second quartile; when the multi-biomarker score is within a range of 0.751 to 1.174, the score is located in the third quartile; and when the multi-biomarker score is within a range of 1.175 to 1.669, the score is located in the fourth quartile.

In an exemplary embodiment, when the score is located in the first quartile, the probability of an acute phase remission is less than 30%.

In an exemplary embodiment, when the score is located in the second quartile, the probability of an acute phase remission increases 1.68 times compared to the first quartile, when the score is located in the third quartile, the probability of an acute phase remission increases 2.34 times compared to the first quartile, and when the score is located in the fourth quartile, the probability of an acute phase remission increases 3.44 times compared to the first quartile.

In addition, the present invention provides a diagnostic kit for predicting antidepressant treatment response and acute prognosis, including an antidepressant treatment response prediction biomarker measurement unit configured to measure a concentration of each of one or more biomarkers contained in a biological sample of a depressed patient, the one or more biomarkers being selected from the group consisting of a high-sensitivity C-reactive protein (hsCRP), interleukin-1 beta (IL-1β), interleukin-6 (IL-6), and leptin.

In an exemplary embodiment, the measurement unit measures the concentration of the hsCRP using a monoclonal antibody against hsCRp, the concentrations of the IL-1β and IL-6 using a high-sensitivity T-cell magnetic bead panel or ELISA, and the concentration of the leptin using ELISA.

In an exemplary embodiment, the biological sample of the depressed patient is serum.

In an exemplary embodiment, the diagnostic kit is a microarray.

According to the present invention, it is confirmed that whether the concentration of one or more markers below a specific concentration selected from the group consisting of a high-sensitivity C-reactive protein (hsCRP), interleukin-1 beta (IL-1β), interleukin-6 (IL-6), and leptin present in biological samples of depressed patients at baseline can be used as a biomarker for predicting antidepressant treatment response and acute prognosis, thereby providing a biomarker that can relatively accurately determine a probability of acute phase remission in depressed patients at the baseline before the administration of antidepressants.

In addition, a method according to the present invention enables the prediction and/or diagnosis of the possibility of predicting antidepressant treatment response and acute prognosis a baseline before antidepressant administration by specifying one or more biomarkers and cutoff levels for predicting antidepressant treatment response and acute prognosis and can thus contribute to the decision-making process of the doctor with regard to therapeutic treatment strategy.

Moreover, a diagnostic kit according to the present invention enables the prediction and/or diagnosis of the possibility of predicting antidepressant treatment response and acute prognosis by measuring a concentration of one or more antidepressant treatment response prediction biomarkers contained in a biological sample of a depressed patient at baseline, and providing a customized treatment strategy to each patient based on the prediction result, thus providing clinical usefulness.

The effects of the present invention are not limited to the foregoing, and it is to be understood that other objects not mentioned herein can be clearly anticipated by those skilled in the art from the following description.

BRIEF DESCRIPTION OF THE DRAWING

FIGURE shows a flow chart depicting participant flow by treatment steps and antidepressants used for 12-week remission.

DETAILED DESCRIPTION

The terminology used in the present invention is merely used to describe particular embodiments, and is not intended to limit the present invention. As used herein, the singular forms are intended to include the plural forms as well, unless the context clearly indicates otherwise. It will be understood that the terms "comprise", "include", "have", etc. when used in this specification specify the presence of stated features, integers, steps, operations, elements, components, or combinations thereof, but do not preclude the presence or addition of one or more other features, integers, steps, operations, elements, components, or combinations thereof.

It will be further understood that, although terms such as "first", "second", etc. may be used herein to describe various elements, these elements are not to be limited by these terms. These terms are only used to distinguish one element from another element. For instance, a "first" element discussed below could be termed a "second" element without departing from the scope of the present invention. Similarly, the "second" element could also be termed a "first" element.

Unless otherwise defined, all terms including technical and scientific terms used herein have the same meanings as those commonly understood by one of ordinary skill in the art to which the present invention belongs. It will be further understood that the terms used herein should be interpreted as having meanings consistent with their meanings in the context of this specification and the relevant art, and are not to be interpreted in an idealized or overly formal sense unless expressly so defined herein.

In interpreting elements, it is to be understood that an error range is included even if there is no separate description thereof.

In the case of a description of a temporal relationship, for example, when the temporal relationship is described as 'after', 'following', 'subsequently, 'before', etc., this includes non-consecutive cases, unless 'immediately or 'directly' is used.

As used herein, the term "diagnosis" means identifying the presence or characteristic of a pathological condition. With regard to the purpose of the present invention, "diagnosis" means determining an antidepressant treatment response and acute prognosis for depressed patients receiving drug therapy based on in vitro analysis of a biological sample of depressed patients at baseline, in which the acute prognosis means the probability of remission occurring within 12 weeks from the baseline.

As used herein, the term "biomarker" means a substance that may indicate a disease state. In the context of the present invention regarding the diagnosis of predicting antidepressant treatment response and acute prognosis in depressed patients, the "biomarker" means that at least one selected from the group consisting of a high-sensitivity C-reactive protein (hsCRP), interleukin-1 beta (IL-1β), interleukin-6 (IL-6), and leptin has a concentration below the preset cut-off level. Among depressed patients at baseline, as the number of the biomarkers increases, the probability of acute phase remission for depressed patients receiving drug therapy increases compared to patients with a reference level without any biomarkers.

As used herein, the term "cutoff level" or "the preset cutoff level" means the relative or absolute level determined to distinguish between individuals with the potential for remission within 12 weeks from the baseline of depressed patients receiving drug therapy. The cutoff level can be given as a value expressed as a fold difference in the case of a relative level or as a concentration for example in the case of an absolute value. As pointed out herein, depending on the biomarker, values below the cut-off level are considered to determine the probability of remission within 12 weeks at baseline.

As used herein, the term "reference level" refers to a state in which there is no biomarker in a biological sample of a depressed patient at baseline. That is, it means a state in which all of the above-mentioned four biomarker concentrations are above the cutoff level determined for each biomarker.

As used herein, the term "predicting" refers to discovering an individual with a high probability of remission due to an excellent treatment response or an individual with a low probability of remission due to a low treatment response during drug therapy.

As used herein, the term "biological sample" includes various types of samples obtained from an individual, and may also be used in diagnosis or monitoring analysis. Biological fluid samples include blood, cerebrospinal fluid (CSF), urine, and other liquid samples of biological origin. For example, the sample may be pretreated for concentration and separation, if necessary.

As used herein, the term "blood" includes whole blood, serum and plasma.

As used herein, the term "individual" is a mammal, preferably a human, and the terms "individual" and "subject" may be used interchangeably in the present invention.

As used herein, the term "baseline" refers to the time point at which initial medical treatment for drug therapy is performed for a depressed patient.

Hereinafter, a detailed description will be given of the technical configuration of the present invention with reference to the accompanying drawings and exemplary embodiments.

However, the present invention is not limited to the embodiments described herein, and may be embodied in other forms. Throughout the specification, the same reference numerals used to explain the present invention designate the same elements.

The present inventors have ascertained that the concentration of one or more of high-sensitivity C-reactive protein (hsCRP), interleukin-1 beta (IL-1β), interleukin-6 (IL-6), and leptin below the cut-off level in biological samples from depressed patients at baseline may be used as a biomarker for predicting antidepressant treatment response and acute prognosis in depressed patients. Thus, the present invention provides a method for predicting and/or diagnosing antidepressant treatment response and acute prognosis in depressed patients at the baseline of starting drug therapy using, as a biomarker, the concentration below the cut-off level of one or more of high-sensitivity C-reactive protein (hsCRP), interleukin-1 beta (IL-1β), interleukin-6 (IL-6), and leptin, and a diagnostic kit.

In the present invention, as described below, the effect of whether the concentration of one or more of high-sensitivity C-reactive protein (hsCRP), interleukin-1 beta (IL-1β), interleukin-6 (IL-6), and leptin in a biological sample of a depressed patient at baseline is below a cut-off level, on the correlation the probability of remission within 12 weeks of the baseline was clearly confirmed.

Therefore, the assessment method for predicting and/or diagnosing antidepressant treatment response and acute prognosis in depressed patients according to the present invention can be classified into a method of measuring one or more biomarkers for predicting the antidepressant treatment response prediction biomarker and a method of measuring all four biomarkers.

The first method includes a measurement step of measuring a concentration of an antidepressant treatment response prediction biomarker contained in a biological sample of a depressed patient at baseline; and a decision step of determining whether there is an acute phase remission, depending on the measured concentration of the antidepressant treatment response prediction marker, and the second method includes a measurement step of measuring a concentration of each of four antidepressant treatment response prediction biomarkers contained in a biological sample of a depressed patient at baseline, the four antidepressant treatment response prediction biomarkers including high-sensitivity C-reactive protein (hsCRP), interleukin-1 beta (IL-1β), interleukin-6 (IL-6), and leptin; and a decision step of determining whether there is an acute phase remission, depending on the measured concentration of each of the four antidepressant treatment response prediction biomarkers.

More specifically, in the first method, to measure antidepressant treatment response prediction biomarkers analyzed in the measurement stage, analyzing at least one biomarker selected from the group consisting of high-sensitivity C-reactive protein (hsCRP), interleukin-1 beta (IL-113), interleukin-6 (IL-6), and leptin is sufficient, but the second method is different only in that all four biomarkers need to be analyzed in the measurement step, and the method of measuring the biomarker concentration in the measurement step in both method may be the same. That is, the analysis method used in the measurement step may include other known methods useful for identifying the presence of a biomarker for predicting and/or diagnosing antidepressant treatment response and acute prognosis in depressed patients. In the present invention, the analysis method may be performed both in vitro and/or in vivo, but preferably the analysis method of the present invention is an in-vitro method based on a sample obtained from an individual and provided in vitro. As such, the biological sample may be selected from among a tissue and a body fluid including blood.

The decision step in both of the first and second method is performed by comparing the concentration of the antidepressant treatment response prediction biomarker measured in the measurement step with a preset cutoff level. But since the first method considers only one or more of the measured biomarker's concentration and the second method consider all four measured biomarker's concentrations, each method is described sequentially.

In the first method, the decision step may be determined that an acute phase remission is likely to occur when one or more of the measured concentration of the biomarker is lower than a preset cutoff level for each biomarker. In the decision step, as the number of the antidepressant treatment response prediction biomarkers is likely to occur increases, the probability of an acute phase remission increases compared to a reference level. It was experimentally confirmed that when the number of the antidepressant treatment response prediction biomarkers, each exhibiting the concentration lower than the preset cutoff level thereof, is one, the probability of an acute phase remission increases 2.3 times compared to the reference level, when the number of the antidepressant treatment response prediction biomarkers is two, the probability of an acute phase remission increases 3.3 times compared to the reference level, when the number of the antidepressant treatment response prediction biomarkers is three, the probability of an acute phase remission increases 3.2 times compared to the reference level, and when the number of the antidepressant treatment response prediction biomarkers is four, the probability of an acute phase remission increases 7.5 times compared to the reference level. Here, the cutoff level of each biomarker is determined through an experiment as described later and has a different value depending on the type of antidepressant treatment response prediction biomarker. That is, when the antidepressant treatment response prediction biomarker is the hsCRP, the preset cutoff level is 0.61 mg/dL, when the antidepressant treatment response prediction biomarker is the IL-1β, the preset cutoff level is 1.13 pg/mL, when the antidepressant treatment response prediction biomarker is the IL-6, the preset cutoff level is 1.45 pg/mL, and when the antidepressant treatment response prediction biomarker is the leptin, the preset cutoff level is 4.39 ng/mL. The results obtained in the decision step of the first method show that the assessment method of this invention is sufficiently meaningful in that it can predict the possibility of the acute phase remission 2.3 times or more than the reference level even if only one biomarker is considered. However, considering all four biomarkers, it is shown that the probability of the acute phase remission improved by 7.5 times compared to the reference level can be predicted. Therefore, it can be seen that performing the second method can more accurately predict the antidepressant treatment response and acute prognosis in depression patients receiving drug therapy at the baseline and obtain significant results.

In the second method, the decision step needs to consider all four biomarkers, thus the decision step includes a reference point allocation step, a calculation step and a determination step. In the reference point allocation step, for each of the respective measured concentrations of the four antidepressant treatment response prediction biomarkers, a reference point of 1 is allocated when the measured concentration is lower than the preset cutoff level thereof and a reference point of 0 is allocated when the measured concentration is higher than the preset cutoff level thereof. The calculation step calculates a multi-biomarker score according to Formula 1 below.

$$\text{multi-biomarker score}=0.694\times A+0.424\times B+0.056\times C+0.495\times D \quad \text{[Formula 1]}$$

wherein A is the reference point of the hsCRP, B is the reference point of the IL-1β, C is the reference point of the IL-6, and D is the reference point of the leptin. In the determination step, a probability of an acute phase remission is determined by finding a quartile in which the calculated total score is located.

Here, the preset cutoff level of each antidepressant treatment response prediction biomarker is the same as described above. Therefore, the measured concentrations of four antidepressant treatment response prediction biomarkers are compared with the cutoff level, and each reference score is given, and then multi-biomarker score can be calculated according to Formula 1. When the multi-biomarker score is within a range of 0 to 0.480, the score is located in the first quartile, when the multi-biomarker score is within a range of 0.481 to 0.750, the score is located in the second quartile, when the multi-biomarker score is within a range of 0.751 to 1.174, the score is located in the third quartile, and when the multi-biomarker score is within a range of 1.175 to 1.669, the score is located in the fourth quartile. As a result, the possibility of an acute phase remission can be more accurately predicted depending on where it is located in the first to fourth quartiles, i.e., the multi-biomarker score.

In other words, it was confirmed that when the score is located in the first quintile, the probability of an acute phase remission is less than 30%, when the score is located in the second quartile, the probability of an acute phase remission increases 1.68 times compared to the first quartile, when the score is located in the third quartile, the probability of an acute phase remission increases 2.34 times compared to the first quartile, and when the score is located in the fourth quartile, the probability of an acute phase remission increases 3.44 times compared to the first quintile.

In addition, the present invention pertains to a diagnostic kit for predicting antidepressant treatment response and acute prognosis in depressed patients, which is used to determine a treatment strategy by predicting antidepressant treatment response and acute prognosis in depressed patients before receiving drug therapy at baseline. The diagnostic kit of the present invention includes a biomarker measurement unit configured to measure the concentration of one or more biomarkers contained in a biological sample of a depressed patient, the one or more biomarkers being selected from the group consisting of high-sensitivity C-reactive protein (hsCRP), interleukin-1 beta (IL-1β), interleukin-6 (IL-6), and leptin.

Here, the biomarker measurement unit measures the concentration of each of the biomarkers using a high-sensitivity bead panel utilizing antigen-antibody reactions, ELISA, ECLISA, or an enzymatic method, etc. In one embodiment, the concentration of the hsCRP using a monoclonal antibody against hsCRP, the concentrations of the IL-1β and IL-6 using a high-sensitivity T-cell magnetic bead panel or ELISA, and the concentration of the leptin using ELISA.

In the diagnostic kit for predicting antidepressant treatment response and acute prognosis in depressed patients of the present invention, it can be judged that the probability of an acute phase remission of patient whose concentration of one or more of high-sensitivity C-reactive protein (hsCRP), interleukin-1 beta (IL-1β), interleukin-6 (IL-6), and leptin are found to be below the cut-off level, is more than 2.3 times higher than the reference level.

The biological sample of the depressed patient used in the diagnostic kit for predicting antidepressant treatment response and acute prognosis in depressed patients of the present invention may be serum. Also, the diagnostic kit may be implemented in a microarray.

In addition, antidepressants may be most known pharmaceuticals, as described below, bupropion, desvenlafaxine, duloxetine, escitaloproam, fluoxetine, mirtazapine, paroxetine, sertraline, venlafaxine and vortioxetine were used. Augmenting drugs, including buspirone, lithium, triiodothyronine, and atypical antipsychotics such as aripiprazole, risperidone, olanzapine, quetiapine, and ziprasidone, were used in the experiment as enhancement drugs.

Example

1. Research Subject

We hypothesized that simultaneous identification of multiple biomarkers covering distinctive functional systems could draw more useful information for predicting pharmacological treatment responses and for clinical decision support with a view to personalized medicine. Using data from a prospective study of Korean patients with depressive disorder, we aimed to develop and evaluate a multi-modal biomarker panel for predicting 12-week remission in a naturalistic sample of patients with depressive disorders receiving a stepwise psychopharmacotherapy protocol in routine care.

2. Blood Biomarkers for Depression Treatment Outcomes

Identifying biomarkers for early prediction of antidepressant treatment outcomes is one option for increasing remission rates through more personalized approaches. Among possible biomarkers, those from peripheral blood assays have advantages of accessibility, cost-effectiveness, and ease of collection in routine clinical practice. A variety of peripheral blood biomarkers representing pertinent functional systems have been evaluated. Of these, markers of immune function have most frequently been investigated, including high-sensitivity C-reactive protein (hsCRP), pro-inflammatory cytokines including tumor necrosis factor-alpha (TNF-α), interleukin-1 beta (IL-1β), IL-6, etc., and anti-inflammatory cytokines including IL-4, IL-10, etc. Metabolic biomarkers evaluated for antidepressant treatment responses include leptin, ghrelin, lipids, and glucose. Of biomarkers related to neurogenic or neuroplastic function, brain-derived neurotrophic factor (BDNF) has been the most frequently studied. Neurotransmitters investigated have been mostly serotonin-related. Endocrine biomarkers evaluated have included mostly cortisol. Nutritional biomarkers studied have included folate, homocysteine, and fatty acid.

3. Research Method

This defined a priori and comprised the primary component of the MAKE Biomarker discovery for Enhancing anTidepressant Treatment Effect and Response (MAKE BETTER) project, which intends to develop a treatment-response prediction index composed of biomarkers for patients with depressive disorders. Study details have been published as a protocol paper and registered with cris.nih.go.kr (identifier: KCT0001332). To reflect real-world settings, participants enrolment and treatment interventions were conducted in a naturalistic fashion. This study was approved by the Chonnam National University Hospital Institutional Review Board (CNUH 2012-014).

The Eligibility Criteria of MAKE BETTER Project

Inclusion criteria were: i) aged older than 7 years; ii) diagnosed with major depressive disorder (MDD), dysthymic disorder, or depressive disorder not otherwise specified (NOS), using the Mini-International Neuropsychiatric Interview (MINI) (Sheehan et al., 1998), a structured diagnostic psychiatric interview based on the Diagnostic and Statistical Manual of Mental Disorders, Fourth Edition (DSM-IV) criteria (APA, 1994); iii) Hamilton Depression Rating Scale (HAMD) (Hamilton, 1960) score 14; iv) able to complete questionnaires, understand the object of the study, and sign the informed consent form. Exclusion criteria were as follows: i) unstable or uncontrolled medical condition; ii) unable to complete the psychiatric assessment or comply with the medication regimen, due to a severe physical illness; iii) current or lifetime DSM-IV diagnosis of bipolar disorder, schizophrenia, schizoaffective disorder, schizophreniform disorder, psychotic disorder NOS, or other psychotic disorder; iv) history of organic psychosis, epilepsy, or seizure disorder; v) history of anticonvulsant treatment; vi) hospitalization for any psychiatric diagnosis apart from depressive disorder (e.g., alcohol/drug dependence); vii) electroconvulsive therapy received for the current depressive episode; viii) pregnant or breastfeeding.

4. Participants

Patients with depressive disorders who fulfilled the eligibility criteria were consecutively recruited from March 2012 to April 2017 from those who had visited the outpatient psychiatric department of CNUH. All inclusion instances represented new treatment episodes—i.e., taking newly initiated antidepressant treatment without any prior medication—whether depressive symptoms were first-onset or recurrent. All patients gave written informed consent to participate in the study and use their data. Participants under the age of 16 obtained the written consent of a parent or legal guardian, and the participant's written consent was obtained.

5. Baseline Characteristics (1) Serum Biomarkers

Participants were instructed to fast from the night before for morning blood sampling, and to sit for 25-45 min quietly and relax before blood samples were acquired. Serum samples were separated and immediately frozen at −80° C. at clinical laboratories of the CNUH. All laboratory measurements were conducted by the Global Clinical Central Lab (Yongin, Korea) blind to patients' status. Fourteen blood biomarkers representing six functional systems were selected based upon existing evidence and were measured using the following methods:

i) Immune
- hsCRP: Tina-quant C-reactive protein (latex) high sensitive assay (Roche, Vilvoorde, Belgium).
- TNF-α: Quantikine® HS ELISA Human TNF-α Immunoassay (R&D Systems, Minneapolis, USA).
- IL-1β, IL-6, IL-4, and IL-10: Human High Sensitivity T Cell Magnetic Bead Panel (EMD Millipore, Billerica, USA).

ii) Metabolic
- leptin: Human Leptin ELISA (BioVendor Laboratory Medicine, Inc., Modrice, Czech Republic).
- ghrelin: GHRELIN (Total) radioimmunoassay kit (EMD Millipore, Billerica, USA).
- total cholesterol: L-type CHO M cholesterol oxidase method kit (Wako Pure Chemical Industries, Osaka, Japan).

iii) Neurogenic or Neuroplastic
- BDNF: Quantikine® ELISA Human BDNF Immunoassay (R&D Systems Inc., Minneapolis, USA).

iv) Neurotransmitter
- serotonin: ClinRep high-performance liquid chromatography kit (Recipe, Munich, Germany).

v) Endocrine
- cortisol: Cobas Cortisol II electrochemiluminescence Immunoassay (Roche, Vilvoorde, Belgium).

vi) Nutritional
- folate: Cobas Elecsys Folate III electrochemiluminescence Immunoassay (Roche, Vilvoorde, Belgium).
- homocysteine: ARCHITECT Homocysteine 1L71 Kit (Abbot, Wiesbaden, Germany).

(2) Covariates

Data on the following socio-demographic characteristics were obtained: age, sex, duration of education, marital status (currently married or not), cohabitation status (living alone or not), religion (religious observance or not), occupational state (current employed or not), and monthly income (above or below 2,000 USD). Clinical characteristics assessed comprised diagnoses of depressive disorders (MDD or other depressive disorders) with certain specifiers including melancholic and atypical features, onset age and illness duration, number of previous depressive episodes, duration of present episode, family history of depression, number of concurrent physical disorders (applying a questionnaire asking for 15 systems or diseases). Assessment scales for investigating symptoms were administered. Depressive and anxiety symptoms were evaluated by the Hospital Anxiety Depression Scale-depression subscale (HADS-D) and anxiety subscale (HADS-A), respectively; quality of life by the EuroQol-5D (EQ-5D); and functioning levels by the Social and Occupational Functioning Assessment Scale (SOFAS). Higher scores on HADS-D and HADS-A, but lower scores on EQ-5D and SOFAS indicate more severe symptomatology.

6. Stepwise Pharmacotherapy

Treatment steps and strategies have been previously described in detail (J Affect Disord 2020; 274:315-25). Before the treatment commencement, a comprehensive examination was conducted for patients' clinical manifestations, illness severity, physical comorbidities and medication lists, and history of prior treatments. In the first step, patients received antidepressant medication (see FIG. 1 legends), considering these patient data and existing treatment guidelines for 3 weeks. General effectiveness and tolerability were evaluated for going ahead with next-step measurement-based treatments. In cases of inadequate improvement or intolerable adverse events, patients were directed to choose whether they would prefer to stay in the present step or get in the next step treatment with switching antidepressants (S), augmenting with other drugs (A), combination of other antidepressants (C), S+A, S+C, A+C, and S+A+C strategies. For settling treatment strategies, patient's opinion was given priority.

7. Definition of Remission

Remission status was assessed at the acute treatment phase (at 3, 6, 9, and 12 weeks). At each assessment point, remission was defined as a HAMD score ≤7. For the 12-week remission status, patients evaluated at least once after baseline to 12 weeks comprised the analyzed sample. Achievement of 12-week remission was defined only when this was maintained up to the 12-week assessment points.

8. Statistical Analysis

Baseline data on socio-demographic and clinical characteristics, and assessment scales were compared by 12-week remission status using t-tests or $\chi^2$ tests as appropriate.

Covariates for further adjusted analyses were selected from those characteristics significantly associated with remission status (P<0.05) and other variables with potential effects on remission, and considering collinearity between the variables. Baseline scores on the HADS-D rather than the HAMD were considered as one of the potential covariates to avoid over adjustment. For estimating the individual associations, baseline serum biomarker levels were compared by the 12-week remission status using Mann-Whitney U tests. For those biomarkers associated at statistical significance (P<0.05), optimal cut-offs with sensitivities, specificities, and positive and negative predictive values were calculated against the 12-week remission status by using the area under receiver operating curve (AUROC) analysis. Odds ratios and 95% confidence intervals (ORs and 95% CIs) for 12-week remission status were estimated by the dichotomized optimal cut-offs of each biomarker using logistic regression analysis after adjustment for relevant covariates.

Effects of multiple biomarkers on remission status were evaluated in two ways. First, summed 0/1 scores from the optimal cut-offs were calculated from the significant biomarkers, and then associations between increased number of biomarkers and remission status were investigated using logistic regression analysis after adjustment for covariates. ORs and 95% CIs were calculated for each group with the 0 score as reference. Second, a continuous multi-biomarker score was estimated using the following equation based on the significant biomarkers: H=(β1×biomarker A)+(β2×biomarkerB), and so on, where β1 and β2 denote the beta coefficients for biomarkers A and B, obtained from the fitted adjusted logistic regression model for remission status. This kind of analytic method was frequently used in longitudinal disease outcome studies.[23] Patients were categorized according to quartiles of this multi-biomarker score and ORs and 95% CIs were calculated for each group with the lowest quartile as reference. Tests for linear trends in ORs were carried out for both approaches: across the summed number of positive biomarkers and the increasing quartiles of the multi-biomarker score. Three additional analyses were conducted: i) the same analytic methods were repeated only in those with MDD; ii) the same analytic methods were conducted for treatment response, defined as a HAMD score reduction of >50% from the baseline; and iii) linear regression analyses were carried out for HAMD score changes with the same adjustment.

Exploratory analyses were carried out to investigate the predictive values of multi- and individual biomarkers for remission status according to each treatment step during the treatment period by using the same logistic regression models. All statistical tests were two-sided with a significance level of 0.05. Statistical analyses were carried out using the SPSS 21.0 and STATA 12.0 software.

9. Result

(1) Recruitment

Patient flow by treatment steps and strategies for the 12-week periods is described in FIG. 1. Of 1262 patients evaluated at baseline, 1094 (86.7%) provided a blood sample, and 1086 (86.1%) were followed at least once during the 12-week treatment period. There were no statistical differences in any baseline characteristic between the 1086 patients included and the remaining 176 participants (all P>0.1).

(2) Baseline Characteristics by Remission Status

Remission was achieved in 490 (45.1%) of the 1086 evaluated during the 12-week phase. Baseline characteristics are compared by 12-week remission status in Table 1. Achievement of 12-week remission was significantly associated with older age, higher monthly income, older age at onset, shorter duration of present episode, lower scores on HADS-D and HADS-A, and higher scores on EQ-5D and SOFAS. Considering the present and previous findings, and collinearity between the variables, eight variables were selected as covariates for the later adjusted analysis: age, sex, marital status, monthly income, number of depressive episodes, duration of present episode, scores on HADS-A and EQ-5D

TABLE 1

| | Up to 12-week treatment (N = 1086) | | | |
|---|---|---|---|---|
| | Remission (N = 490) | No remission (N = 596) | Statistical coefficients[a] | P-value |
| **Socio-demographic characteristics** | | | | |
| Age, mean (SD) years | 58.2 (13.9) | 55.9 (15.6) | t = −2.610 | **0.009** |
| Sex, N (%) female | 334 (68.2) | 411 (69.0) | $X^2$ = 0.079 | 0.778 |
| Education, mean (SD) years | 9.1 (4.9) | 9.1 (4.7) | t = +0.065 | 0.948 |
| Marital status, N (%) unmarried | 134 (27.3) | 192 (32.2) | $X^2$ = 3.033 | 0.082 |
| Living alone, N (%) | 73 (14.9) | 94 (15.8) | $X^2$ = 0.158 | 0.691 |
| Religious observance, N (%) | 281 (57.3) | 326 (54.7) | $X^2$ = 0.765 | 0.382 |
| Unemployed status, N (%) | 130 (26.5) | 186 (31.2) | $X^2$ = 2.852 | 0.091 |
| Monthly income, N (%) <2,000 USD | 273 (55.7) | 375 (62.9) | $X^2$ = 5.801 | **0.016** |
| **Clinical characteristics** | | | | |
| Major depressive disorder, N (%) | 415 (84.7) | 510 (85.6) | $X^2$ = 0.164 | 0.686 |
| Melancholic feature, N (%) | 67 (13.7) | 95 (15.9) | $X^2$ = 1.088 | 0.297 |
| Atypical feature, N (%)) | 34 (6.9) | 35 (5.9) | $X^2$ = 0.514 | 0.473 |
| Age at onset, mean (SD) years | 53.6 (15.7) | 50.5 (17.3) | t = +3.042 | **0.002** |
| Duration of illness, mean (SD) years | 4.7 (8.7) | 5.4 (9.3) | t = −1.311 | 0.190 |
| Number of depressive episodes, mean (SD) | 1.0 (1.4) | 1.2 (1.5) | t = −1.836 | 0.067 |
| Duration of present episode, mean (SD) months | 6.4 (8.0) | 8.3 (12.0) | t = −3.128 | **0.002** |

TABLE 1-continued

| | Up to 12-week treatment (N = 1086) | | | |
|---|---|---|---|---|
| | Remission (N = 490) | No remission (N = 596) | Statistical coefficients[a] | P-value |
| Family history of depression, N (%) | 76 (15.5) | 82 (13.8) | $X^2$ = 0.664 | 0.415 |
| Number of physical disorders, mean (SD) | 1.7 (1.2) | 1.6 (1.3) | t = +1.212 | 0.226 |
| Assessment scales, mean (SD) scores | | | | |
| Hospital Anxiety & Depression Scale-depression subscale | 20.4 (4.1) | 21.0 (4.1) | t = −2.418 | 0.016 |
| Hospital Anxiety & Depression Scale-anxiety subscale | 11.3 (4.1) | 12.2 (4.0) | t = −3.666 | **<0.001** |
| EuroQol-5D | 0.69 (0.2) | 0.66 (0.2) | t = +2.504 | **0.012** |
| Social and Occupational Functional Assessment Scale | 57.1 (7.1) | 55.0 (7.6) | t = +4.785 | **0.001** |

[a]Independent two sample t-test or $X^2$ tests, as appropriate.
Bold style denotes statistical significance.

(3) Individual Associations Between Serum Biomarkers and Remission Status

Baseline levels of serum biomarkers are compared by 12-week remission status in Table 2. Achievement of 12-week remission was significantly associated with lower levels of hsCRP, IL-1β, IL-6, and leptin, and with higher folate levels. For these biomarkers showing statistical significance, optimal cut-offs with sensitivities, specificities, and positive and negative predictive values were obtained by AUROC analysis (Table 3). In the logistic regression analysis after adjustment for eight covariates above, achievement of 12-week remission was independently associated with below cut-off levels of hsCRP, IL-1β, IL-6, and leptin.

TABLE 2

| | Up to 12-week treatment (N = 1086) | | | |
|---|---|---|---|---|
| | Remission (N = 490) | No remission (N = 596) | U-value[a] | P-value |
| High-sensitivity C-reactive protein, mg/L | 0.4 (0.9) | 0.6 (1.2) | 116690.5 | **<0.001** |
| Tumor necrosis factor-α, pg/mL | 0.6 (0.4) | 0.6 (0.5) | 137231.5 | 0.088 |
| Interleukin-1β, pg/mL | 1.1 (0.5) | 1.2 (0.9) | 118872.5 | **<0.001** |
| Interleukin-6, pg/mL | 1.6 (1.5) | 1.7 (1.7) | 134480.5 | **0.025** |
| Interleukin-4, pg/mL | 35.5 (35.5) | 38.4 (38.4) | 136898.5 | 0.076 |
| Interleukin-10, pg/mL | 10.2 (9.8) | 11.0 (9.6) | 138658.0 | 0.152 |
| Leptin, ng/mL | 5.3 (5.8) | 6.1 (6.6) | 124592.0 | **<0.001** |
| Ghrelin, pg/mL | 389.5 (177.5) | 370.0 (180.8) | 152450.0 | 0.211 |
| Total cholesterol, mg/dL | 177.0 (52.3) | 177.0 (53.0) | 146598.5 | 0.910 |
| Brain derived neurotrophic factor, ng/mL | 23.3 (8.8) | 23.1 (8.6) | 147203.5 | 0.818 |
| Serotonin, ng/mL | 74.7 (67.3) | 70.1 (69.5) | 154263.0 | 0.109 |
| Cortisol, μg/dL | 10.9 (5.8) | 10.5 (5.6) | 149270.5 | 0.527 |
| Folate, ng/mL | 7.7 (6.3) | 7.1 (5.9) | 157265.0 | **0.029** |
| Homocysteine, μmol/L | 11.1 (4.7) | 10.9 (4.7) | 150484.5 | 0.385 |

[a]Mann-Whitney U tests.

Bold style denotes statistical significance.

TABLE 3

| | Up to 12-week treatment (N = 1086) | | | | | |
|---|---|---|---|---|---|---|
| | Optimal cut-off | OR (95% CI) | Sensitivity | Specificity | Positive predictive value | Negative predictive value |
| High-sensitivity C-reactive protein | <0.61 mg/dL | 2.05 (1.59-2.66) | 48.0% | 69.8% | 52.6% | 66.3% |
| Tumor necrosis factor-α | — | — | — | — | — | — |
| Interleukin-1β | <1.13 pg/mL | 1.61 (1.25-2.07) | 53.4% | 51.5% | 53.4% | 62.0% |
| Interleukin-6 | <1.45 pg/mL | 1.31 (1.02-1.69) | 60.9% | 46.5% | 49.5% | 58.1% |
| Leptin | <4.39 ng/mL | 1.68 (1.30-2.17) | 67.6% | 44.1% | 52.8% | 59.5% |
| Brain derived neurotrophic factor | — | — | — | — | — | — |
| Folate | >6.60 ng/mL | 1.16 (0.90-1.49) | 61.0% | 44.3% | 47.4% | 58.0% |

Optimal cut-off values were obtained from the receiver operating characteristic curve.
Odds ratios (95% confidence intervals) [OR (95% CI)] were estimated by using logistic regression analyses after adjustment for age, sex, marital status, monthly income, number of depressive episodes, duration of present episode, scores on Hospital Anxiety & Depression Scale-anxiety subscale and EuroQol-5D.

(4) Multiple Biomarkers and Treatment Outcomes

Achievement of 12-week remission according to the increased number of biomarkers below cut-offs are described in the upper part of Table 4 and Table 5. The probability of remission increased incrementally with the increasing number of favourable biomarkers (all P-values for trend <0.001). Compared to the patients without any favourable biomarkers, the ORs (95% CIs) of those with 4 favourable biomarkers were 7.49 (4.11-13.65) for achievement of 12-week remission in the same logistic regression model. Achievement of remission according to quartiles of multi-biomarker scores are described in the lower part of Table 4 and Table 5.

TABLE 4

| | Up to 12-week treatment (N = 1086) | | | |
|---|---|---|---|---|
| | N | Remission, N (%) | OR (95% CI) | P-value for trend |
| Number of serum biomarkers[a] | | | | |
| 0 | 131 | 28 (21.4) | Reference | <0.001 |
| 1 | 260 | 102 (39.2) | 2.30 (1.40-3.77) | |
| 2 | 350 | 170 (48.6) | 3.33 (2.07-5.46) | |
| 3 | 241 | 118 (49.0) | 3.17 (1.93-5.22) | |
| 4 | 104 | 72 (69.2) | 7.49 (4.11-13.65) | |
| Quartiles of multi-biomarker scores[b] | | | | |
| 1 (lowest) | 275 | 80 (29.1) | Reference | <0.001 |
| 2 | 259 | 107 (41.3) | 1.68 (1.17-2.43) | |
| 3 | 298 | 152 (51.0) | 2.34 (1.65-3.33) | |
| 4 | 254 | 151 (59.4) | 3.44 (2.37-4.97) | |

Odds ratios (95% confidence intervals) [OR (95% CI)] were estimated by using logistic regression analyses after adjustment for age, sex, marital status, monthly income, number of depressive episodes, duration of present episode, scores on Hospital Anxiety & Depression Scale-anxiety subscale and EuroQol-5D.
[a]For calculating the number of serum biomarkers, 0 (unfavourable) or 1 (favourable) score from the optimal cut-offs of each significant biomarker was generated, and then summed scores were estimated ranging from 0 to 4, with higher scores indicating more favourable condition.
[b]For calculating the continuous multi-biomarker scores, the following equations were used: 12-week remission = (0.694 × high-sensitivity C-reactive protein) + (0.424 × interleukin-1β) + (0.056 × interleukin-6) + (0.495 × leptin). Then, quartiles of the multi-biomarker scores were generated ranging from 1 to 4, with higher scores indicating more favourable condition.

TABLE 5

| | Up to 12-week treatment (N = 925) | | | |
|---|---|---|---|---|
| | N | Remission, N (%) | OR (95% CI) | P-value for trend |
| Number of serum biomarkers[a] | | | | |
| 0 | 109 | 24 (22.0) | Reference | <0.001 |
| 1 | 217 | 83 (38.2) | 2.19 (1.29-3.73) | |
| 2 | 310 | 152 (49.0) | 3.41 (2.06-5.65) | |
| 3 | 203 | 99 (48.8) | 3.37 (1.98-5.73) | |
| 4 | 86 | 57 (66.3) | 6.96 (3.68-13.16) | |
| Quartiles of multi-biomarker scores[b] | | | | |
| 1 (lowest) | 238 | 71 (29.8) | Reference | <0.001 |
| 2 | 209 | 84 (40.2) | 1.58 (1.07-2.34) | |
| 3 | 267 | 138 (51.7) | 2.52 (1.74-3.63) | |
| 4 | 211 | 122 (57.8) | 3.22 (2.18-4.76) | |

Odds ratios (95% confidence intervals) [OR (95% CI)] were estimated by using logistic regression analyses after adjustment for age, sex, marital status, monthly income, number of depressive episodes, duration of present episode, scores on Hospital Anxiety & Depression Scale-anxiety subscale and EuroQol-5D.
[a]For calculating the number of serum biomarkers, 0 (unfavourable) or 1 (favourable) score from the optimal cut-offs of each significant biomarker was generated, and then summed scores were estimated ranging from 0 to 4, with higher scores indicating more favourable condition.
[b]For calculating the continuous multi-biomarker scores, the following equations were used: 12-week remission = (0.694 × high-sensitivity C-reactive protein) + (0.424 × interleukin-1β) + (0.056 × interleukin-6) + (0.495 × leptin); Then, quartiles of the multi-biomarker scores were generated ranging from 1 to 4, with higher scores indicating more favourable condition.

The probability of remission likewise increased incrementally with the higher quartile of multi-biomarker scores (all P-values for trend <0.001). The ORs (95% CIs) for the highest vs. lowest quartile of multi-biomarker scores were 3.44 (2.37-4.97) for achievement of 12-week remission in the same logistic regression model. Additionally, the ORs (95% CIs) for the highest quartile of multi-biomarker scores compared to patient without any favourable biomarkers were 5.39 (3.31-8.78) for achievement of 12-week remission. Findings restricted to patients with MDD were similar to those with total sample (Table 5). Results on treatment responses and HAMD score changes shown similar trends (Tables 6 and 7).

TABLE 6

| | N | Response, N (%) | OR (95% CI) | P-value for trend |
|---|---|---|---|---|
| | Up to 12-week treatment (N = 1086) | | | |
| Number of serum biomarkers | | | | |
| 0 | 131 | 59 (45.0) | Reference | <0.001 |
| 1 | 260 | 143 (55.0) | 1.49 (0.98-2.28) | |
| 2 | 350 | 224 (64.0) | 2.17 (1.44-3.26) | |
| 3 | 241 | 150 (62.2) | 2.01 (1.31-3.10) | |
| 4 | 104 | 78 (75.0) | 3.66 (2.09-6.42) | |
| Quartiles of multi-biomarker scores | | | | |
| 1 (lowest) | 275 | 138 (50.2) | Reference | <0.001 |
| 2 | 259 | 144 (55.6) | 1.24 (0.88-1.75) | |
| 3 | 298 | 194 (65.1) | 1.85 (1.32-2.59) | |
| 4 | 254 | 178 (70.1) | 2.33 (1.63-3.33) | |

TABLE 7

| | N | β | B (95% CI) | P-value | P-value for trend |
|---|---|---|---|---|---|
| | Up to 12-week treatment (N = 1086) | | | | |
| Number of serum biomarkers | | | | | |
| 0 | 131 | Reference | Reference | — | <0.001 |
| 1 | 260 | −0.17 | −2.10 (−3.30, −0.89) | 0.001 | |
| 2 | 350 | −0.23 | −1.54 (−2.12, −0.96) | <0.001 | |
| 3 | 241 | −0.23 | −0.96 (−1.37, −0.55) | <0.001 | |
| 4 | 104 | −0.35 | −1.12 (−1.50, −0.74) | <0.001 | |
| Quartiles of multi-biomarker scores | | | | | |
| 1 (lowest) | 275 | Reference | Reference | — | <0.001 |
| 2 | 259 | −0.09 | −1.04 (−2.02, −0.07) | 0.037 | |
| 3 | 298 | −0.18 | −1.08 (−1.55, −0.60) | <0.001 | |
| 4 | 254 | −0.25 | −0.97 (−1.30, −0.64) | <0.001 | |

(5) Biomarker Associations by Treatment Steps

Associations of increases in one number of biomarkers and in one quartile of multi-biomarker scores with remission status were summarized in Table 8. The strengths of the associations were most obvious for treatment Step 1 monotherapy but were decreased with increased treatment steps and were no longer statistically significant for treatment Step 4+.

TABLE 8

| | | N | Remission N (%) | One number increase of serum biomarkers: OR (95% CI) | P-value |
|---|---|---|---|---|---|
| Up to 12-week treatment (N = 1086) | | | | | |
| Treatment steps | 1 | 463 | 172 (37.1) | 1.67 (1.43-1.96) | <0.001 |
| | 2 | 360 | 176 (48.9) | 1.49 (1.15-1.91) | 0.002 |
| | 3 | 200 | 106 (53.0) | 1.32 (1.00-1.74) | 0.050 |
| | 4+ | 63 | 36 (57.1) | 1.21 (0.66-2.22) | 0.534 |

TABLE 8-continued

| | | N | Remission N (%) | One number increase of serum biomarkers: OR (95% CI) | P-value |
|---|---|---|---|---|---|
| Up to 12-month treatment (N = 884) | | | | | |
| Treatment steps | 1 | 326 | 214 (65.6) | 1.80 (1.41-2.31) | <0.001 |
| | 2 | 286 | 203 (71.0) | 1.80 (1.15-2.73) | 0.011 |
| | 3 | 172 | 172 (81.4) | 1.77 (1.02-3.27) | 0.043 |
| | 4+ | 100 | 68 (68.0) | 1.13 (0.84-2.52) | 0.507 |

Odds ratios (95% confidence intervals) [OR (95% CI)] were estimated by using logistic regression analyses after adjustment for age, sex, marital status, monthly income, number of depressive episodes, duration of present episode, scores on Hospital Anxiety & Depression Scale-anxiety subscale and EuroQol-5D.

(6) Discussion

In this study of outpatients with depressive disorders following a naturalistic and flexible treatment protocol, combination scores of four serum biomarkers (hsCPR, IL-1β, IL-6, leptin) predicted 12-week remission in a dose dependent manner. Results were similar in three additional analyses: restricted with MDD patients, and outcomes on response and HAMD score changes. These associations were evident for treatment Step 1 monotherapy but were weakened with increased treatment steps and were no longer statistically significant for treatment Step 4+. That is, the associations between serum biomarkers and remission status were most evident in the treatment Step 1 monotherapy and then weakened with increased treatment steps, falling below statistical significance by the treatment Step 4+.

Our Step 1 monotherapy for 12-week remission was similar to previous biomarker studies in study design, hence there could be considerable overlap in the study findings. Disappearance of predictive values of the biomarkers in the treatment step 4+ could be explained by several ways. First, by advances of treatment steps with switching, augmentation, or combination strategies, a particular potential association between an antidepressant and a biomarker could be mitigated and blurred. Second, the patient number was getting smaller with the increased treatment step, and therefore statistical power was reducing. Third, the patients entering into the higher treatment steps, Step 4+ in particular, might have different biological predispositions beyond the biomarkers investigated in the present study.

Nevertheless, based on the findings of the present invention, it can be claimed that patients with unfavourable biomarker state at baseline could have better clinical outcomes if they entered into an alternative pharmacological regime even in the early treatment phase. If this finding could be replicated, this approach might facilitate remission in clinical practice and provide evidence for revised treatment guidelines.

(7) Comparisons with Previous Studies

The study design should be considered in interpreting these findings of the present invention. Most previous studies of biomarkers for antidepressant treatment response have been carried out in short-term (8-12 week) randomised controlled designs for one or two antidepressant monotherapy courses. This approach is helpful to understand particular associations between a biomarker and an antidepressant treatment response. However, the findings have been inconsistent, and the explanatory power has been too small for use in clinical practice. On the other hand, the present invention was designed to reflect usual clinical situations and to improve potential clinical applicability in that treatment steps could be advanced every 3 weeks during the 12-week acute treatment phase with a range of treatment strategies possible considering treatment efficacy and safety, and patient preference. Under these conditions, three inflammatory biomarkers (hsCPR, IL-1β, and IL-6), and a metabolic biomarker (leptin) were identified as independent predictors for 12-week treatment responses out of 14 evaluated biomarkers covering six functional systems. Despite the differences in study design, our findings mainly on inflammatory biomarkers were broadly consistent with those from previous reports, since these markers have been most frequently and extensively investigated of peripheral blood biomarkers for antidepressant treatment responses. Several studies have reported that baseline elevated pro- and/or anti-inflammatory cytokine levels predict decreased antidepressant responses, although some studies have found no such associations. A recent gene expression study demonstrated that IL-1 and other cytokines were elevated in treatment-resistant depression and examined the cumulative predictive value of more than one inflammatory biomarkers. Also, strengths of the present invention were that the sample size was large compared to previous biomarker studies, and participants were evaluated with a structured research protocol and well-recognized and standardized scales. Therefore, the results of the present invention support an extension of the inflammatory hypothesis for antidepressant treatment responses beyond the scenario of randomized clinical trials with monotherapy to more naturalistic clinical practice situations involving polypharmacy. However, considering the anti-inflammatory effects of antidepressants, the mechanism of observed findings needs to be elucidated further.

(8) Predictive Values of Multi-Biomarkers

The sensitivities, specificities, and positive and negative predictive values of individual biomarkers were not satisfactory for clinical application, although their predictive values were statistically significant (Table 3). The most particular finding of the present invention was that biomarkers in combination had significantly better and incremental predictive values for treatment responses. In particular, the OR for 12-week remission in patients with 4 favourable biomarkers was 7.49 compared to those without these, and the OR for the highest vs. lowest quartile groups of multi-biomarker scores was 3.44 for the same outcome (Table 4), which are sizeable improvements for the ORs of individual markers in the 1.3-2.1 range. Many researchers have highlighted the importance of considering multiple biomarkers for prediction of antidepressant treatment responses, and “omics” approaches might give rise to a solution in this respect, although have shown inconsistent results so far. Predictive values of multiple peripheral blood biomarkers have rarely been evaluated and are not fully understood. In a meta-analysis of inflammation and clinical response to treatment in depression, individual effects of CRP, TNF-α, and IL-6 were not significant, while those of a composite of the three markers were statistically significant particularly in outpatients, which is in keeping with the findings of the present invention. A recent study investigated a panel of peripheral biomarkers in depressive patients receiving antidepressants, concluding that inflammatory biomarkers had potential. However, this study did not evaluate combined effects of the biomarkers. As far as we are aware, the present invention is the first to date to investigate multi-modal effects of blood biomarkers covering various functional systems on pharmacological treatment outcomes of depressive disorders.

Consequently, the present invention can not only contribute to a decision-making process for patient-tailored effective treatment strategies with regard to therapeutic drugs and/or treatment methods before starting drug therapy in depressed patients, but also can be very helpful as a potential tool for treatment of patients with depression.

Although exemplary embodiments of the present invention have been disclosed for illustrative purposes, those skilled in the art will appreciate that various modifications and substitutions are possible without departing from the scope and spirit of the invention as disclosed in the accompanying claims.

What is claimed is:

1. A method for predicting antidepressant treatment response and acute prognosis within 12 weeks from a baseline measurement in a depressed patient being treated with a first antidepressant, the method comprising:

measuring a concentration of each of the four antidepressant treatment response prediction biomarkers, high-sensitivity C-reactive protein (hsCRP), interleukin-1 beta (IL-1β), interleukin-6 (IL-6), and leptin in a biological sample from the patient at baseline, determining whether the patient has a probability of an acute phase remission within 12 weeks, depending on the measured concentration of each of the four antidepressant treatment response prediction biomarkers, comprising:

allocating a reference point for each of the respective measured concentrations of the four antidepressant treatment biomarkers, wherein the reference point is 1 when the measured concentration is less than a preset cutoff level or the reference point is 0 when the measured concentration is greater than a preset cutoff level; calculating a multi-biomarker score according to Formula 1: multi-biomarker score=0.694×A+0.424×B+0.056×C+0.495×D [Formula 1], wherein A is the reference point of the hsCRP, B is the reference point of the IL-1β, C is the reference point of the IL-6, and D is the reference point of the leptin; and determining the probability of an acute phase remission by the calculated total score;

and treating the patient according to the determination, comprising:

(a) continuing treatment with the first antidepressant when it is determined that the depressed patient has the probability of acute phase remission; or (b) when it is determined that the depressed patient lacks the probability of the acute phase remission, treating the depressed patient with at least one selected from the group consisting of: (i) administering a second antidepressant different from the first antidepressant, (ii) administering a combination of antidepressants each different from the first antidepressant, and (iii) administering the first antidepressant with an augmenting drug including a mood stabilizer, a hormone, and/or an antipsychotic drug.

2. The method of claim 1, wherein when the antidepressant treatment response prediction biomarker is the hsCRP, the preset cutoff level is 0.61 mg/dL, when the antidepressant treatment response prediction biomarker is the IL-1β, the preset cutoff level is 1.13 pg/mL, when the antidepressant treatment response prediction biomarker is the IL-6, the preset cutoff level is 1.45 pg/mL, and when the antidepressant treatment response prediction biomarker is the leptin, the preset cutoff level is 4.39 ng/mL.

3. The method of claim 1, wherein the determining the probability of an acute phase remission by the calculating total score comprises finding a quartile in which the calculated total score is located, wherein when the multi-biomarker score is within a range of 0 to 0.480, the score is located in the first quartile;

when the multi-biomarker score is within a range of 0.481 to 0.750, the score is located in the second quartile;

when the multi-biomarker score is within a range of 0.751 to 1.174, the score is located in the third quartile; and when the multi-biomarker score is within a range of 1.175 to 1.669, the score is located in the fourth quartile.

4. The method of claim 3, wherein when the score is located in the first quartile, the probability of an acute phase remission is less than 30%.

5. The method of claim 4, wherein when the score is located in the second quartile, the probability of an acute phase remission increases 1.68 times compared to the first quartile, when the score is located in the third quartile, the probability of an acute phase remission increases 2.34 times compared to the first quartile, and when the score is located in the fourth quartile, the probability of an acute phase remission increases 3.44 times compared to the first quartile.

6. The method of claim 1, wherein each of the first antidepressant and the second antidepressant, the second antidepressant being different from the first antidepressant, is selected from the group consisting of escitalopram, sertraline, paroxetine, fluoxetine, mirtazapine, bupropion, venlafaxine, duloxetine, desvenlafaxine, vortioxetine, and agomelatine, and the augmenting drug including the mood stabilizer, the hormone, and/or the antipsychotic drug is selected from the group consisting of lithium, thyroid hormone, chlorpromazine, perphenazine, loxapine, trifluoperazine, haloperidol, bromperidol, pimozide, sulpiride clozapine, risperidone, olanzapine, and quetiapine.

* * * * *